(12) United States Patent
Singh et al.

(10) Patent No.: US 11,541,012 B1
(45) Date of Patent: Jan. 3, 2023

(54) COMPOSITIONS COMPRISING DISODIUM LEVOFOLINATE

(71) Applicant: Spectrum Pharmaceuticals, Inc., Henderson, NV (US)

(72) Inventors: Ramsharan Singh, Irvine, CA (US); Bahman Shimiaei, Laguna Niguel, CA (US)

(73) Assignee: Acrotech Biopharma, LLC, East Windsor, NJ (US)

(*) Notice: Subject to any disclaimer, the term of this patent is extended or adjusted under 35 U.S.C. 154(b) by 59 days.

(21) Appl. No.: 16/257,684

(22) Filed: Jan. 25, 2019

Related U.S. Application Data

(60) Provisional application No. 62/622,720, filed on Jan. 26, 2018.

(51) Int. Cl.

| | |
|---|---|
| *A61K 9/19* | (2006.01) |
| *A61K 31/519* | (2006.01) |
| *A61K 47/26* | (2006.01) |
| *A61K 47/22* | (2006.01) |
| *A61K 47/18* | (2017.01) |
| *A61K 9/00* | (2006.01) |

(52) U.S. Cl.
CPC ............. *A61K 9/19* (2013.01); *A61K 9/0019* (2013.01); *A61K 31/519* (2013.01); *A61K 47/18* (2013.01); *A61K 47/22* (2013.01); *A61K 47/26* (2013.01)

(58) Field of Classification Search
CPC .... A61K 31/519; A61K 47/26; A61K 9/0019; A61K 9/19
See application file for complete search history.

(56) References Cited

FOREIGN PATENT DOCUMENTS

CN 101185649 * 5/2008

OTHER PUBLICATIONS

Rao et al., Zhongguo Yaoke Daxue Xuebao, 2012, 43(4), 350-354.*

* cited by examiner

*Primary Examiner* — Shobha Kantamneni
(74) *Attorney, Agent, or Firm* — K&L Gates LLP; Louis C. Cullman; Hal Gibson

(57) ABSTRACT

Provided herein are compositions comprising disodium levofolinate. Also provided are processes for preparing compositions comprising disodium levofolinate. Also provided are compositions comprising disodium levofolinate prepared by the processes provided herein. Also provided are methods of treating folic acid deficiency in a subject in need thereof, comprising administering a composition provided herein to the subject. Also provided are methods of treating cancer in a subject in need thereof, comprising administering 5-fluorouracil and a composition provided herein to the subject. Also provided are methods of reducing the immediate toxic effects of methotrexate overdose in a subject in need thereof, comprising administering a composition provided herein to the subject. Also provided are methods of treating cancer in a subject in need thereof, comprising administering high-dose methotrexate and a composition provided herein to the subject. Also provided are methods of treating megaloblastic anemia in a subject in need thereof, comprising administering a composition provided herein to the subject.

15 Claims, 2 Drawing Sheets

COMPOSITIONS COMPRISING DISODIUM LEVOFOLINATE

RELATED APPLICATIONS

This application claims priority to U.S. Provisional Patent Application No. 62/622,720, filed Jan. 26, 2018, the entire content of which is incorporated herein by reference.

SUMMARY

Described herein are compositions comprising disodium levofolinate (i.e., disodium levoleucovorin) and one or more of an additional component(s), which may be considered as an impurity(ies). In some embodiments, the additional components can be one or more of 4-aminobenzoylglutamic acid, folic acid, 10-formylfolic acid, formyltetrahydropteroic acid, diformyltetrahydrofolic acid, 10-formyldihydrofolic acid, 7,8-dihydrofolic acid, methylenetetrahydrofolic acid, tetrahydropteridine-5-oxide, carboxy-leucguan, hydroxyleucovorin or 7,8-dihydroxanthopterin. In some embodiments, the additional components can be not more than three of the enumerated components. In some embodiments, pharmaceutical compositions described herein may comprise a disodium levofolinate and one or two additional components. One of the additional components can be 10-formyldihydrofolic acid. One of the additional components can be 4-aminobenzoylglutamic acid. In some embodiments, the compositions are pharmaceutical compositions. In some embodiments, the compositions are lyophilized compositions. In some embodiments, the compositions are aqueous compositions.

Also described herein are processes to prepare a lyophilized composition including disodium levofolinate. In some embodiments, the process can be accomplished at a temperature of less than about 18° C.

In some embodiments, the compositions described herein can be used in the preparation of a medicament for the treatment of cancer, methotrexate toxicity rescue, or folic acid deficiency.

DETAILED DESCRIPTION

Definitions

Figure 1:
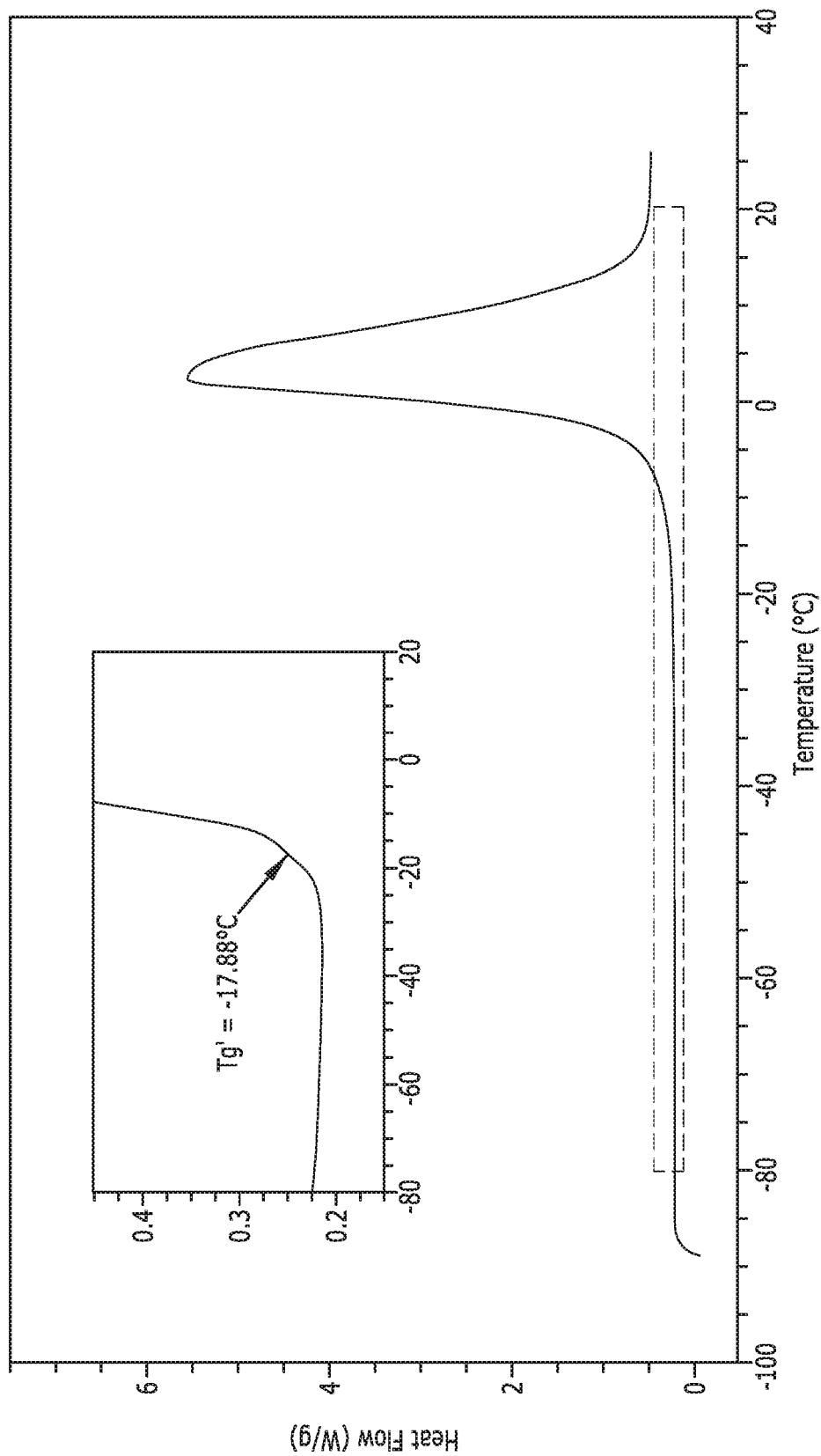
FIG. 1 illustrates a DSC thermogram of disodium levofolinate showing a glass transition occurring at −17.88° C.

Listed below are definitions of various terms used to describe the compositions and methods provided herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which the compositions and methods provided herein pertain. Generally, the nomenclature used herein and the laboratory procedures in pharmaceutical sciences, organic chemistry, and analytical chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed compositions and methods.

As used herein, the terms "effective amount," "pharmaceutically effective amount" and "therapeutically effective amount" refer to a nontoxic but sufficient amount of an agent to provide the desired biological result. That result may be reduction, alleviation, or both, of the signs, symptoms, or causes of a disease, or any other desired alteration of a biological system. An appropriate therapeutic amount in any individual case may be determined by one of ordinary skill in the art using routine experimentation.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the term "treatment" or "treating," is defined as the application or administration of a therapeutic agent, i.e., a compound or composition thereof provided herein, to a subject in need thereof, or application or administration of a therapeutic agent to an isolated tissue or cell line from the subject (e.g., for diagnosis or ex vivo applications). Such treatments may be specifically tailored or modified, based on knowledge obtained from the field of pharmacogenomics.

Compositions

Described herein are compositions comprising disodium levofolinate (e.g., at a concentration of about 50 mg/mL) and one or more additional components. In some embodiments, the additional components can be one or more of 4-aminobenzoylglutamic acid, folic acid, 10-formylfolic acid, formyltetrahydropteroic acid, diformyltetrahydrofolic acid, 10-formyldihydrofolic acid, 7,8-dihydrofolic acid, methylenetetrahydrofolic acid, tetrahydropteridine-5-oxide, carboxy-leucguan, hydroxyleucovorin or 7,8-dihydroxanthopterin. In some embodiments, the additional components can be not more than three of the enumerated components. In some embodiments, pharmaceutical compositions described herein may comprise a disodium levofolinate and one additional component. The additional component can be 10-formyldihydrofolic acid. The 10-formyldihydrofolic acid can be in an amount of about 0.1% to about 0.5% mole fraction. The 10-formyldihydrofolic acid can be in an amount of about 0.5% to about 1.0% mole fraction. The 10-formyldihydrofolic acid can be in an amount of about 0.03% to about 0.1% mole fraction.

In other embodiments, compositions of disodium levofolinate can include about 0.03% to about 0.1% mole fraction of 4-aminobenzoylglutamic acid.

In some embodiments, the compositions described herein may be suitable for injection. Injection can be intramuscular, intravenous, subcutaneous, or a combination thereof.

In some embodiments, the compositions can include additional excipients, such as but not limited to mannitol for acceptable cake formation during freeze-drying. In some embodiments, the compositions can include mannitol at a concentration of about 20 to 40 mg/mL (e.g., 30 mg/mL).

The compositions can have a pH of about 7 to about 8.5, or about 7.4 to about 8.1. The pH of a composition can be adjusted during preparation using an appropriate amount of sodium hydroxide. In some embodiments, when injectable, the compositions can have a pH of about 7.5 to about 8.1. In some embodiments, the pH of the composition is about 7.9.

Disodium levoleucovorin (a.k.a. disodium levofolinate or disodium (2S)-2-[[4-[[(6S)-2-amino-5-formyl-4-oxo-1,6,7,8-tetrahydropteridin-6-yl]methylamino]benzoyl]amino]pentanedioate) is shown below.

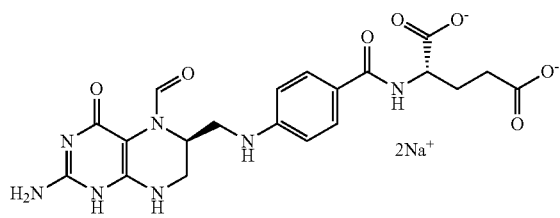 [SMILES: Nc1nc(=O)c2c([nH]1)NC[C@H](CNc1ccc(C(=O)N[C@@H](CCC(=O)[O-])C(=O)[O-])cc1)N2C=O]

Disodium Levoleucovorin

Thus, in one aspect, provided herein are compositions comprising:
a) disodium levofolinate; and
b) one or more of 4-aminobenzoylglutamic acid, folic acid, 10-formylfolic acid, formyltetrahydropteroic acid, diformyltetrahydrofolic acid, 10-formyldihydrofolic acid, 7,8-dihydrofolic acid, methylenetetrahydrofolic acid, tetrahydropteridine-5-oxide, carboxy-leucguan, hydroxyleucovorin or 7,8-dihydroxanthopterin,
wherein the composition comprises not more than about 1% mole fraction (e.g., not more than about 0.9%, 0.8%, 0.7%, 0.6%, 0.5% or 0.4% mole fraction) of the one or more of 4-aminobenzoylglutamic acid, folic acid, 10-formylfolic acid, formyltetrahydropteroic acid, diformyltetrahydrofolic acid, 10-formyldihydrofolic acid, 7,8-dihydrofolic acid, methylenetetrahydrofolic acid, tetrahydropteridine-5-oxide, carboxy-leucguan, hydroxyleucovorin or 7,8-dihydroxanthopterin.

In another aspect, provided herein are compositions comprising:
a) disodium levofolinate;
b) 10-formyldihydrofolic acid; and
c) 4-aminobenzoylglutamic acid,
wherein the 10-formyldihydrofolic acid is not more than about 1% of the mole fraction of the composition.

In yet another aspect, provided herein are compositions comprising:
a) disodium levofolinate;
b) 10-formyldihydrofolic acid; and
c) 4-aminobenzoylglutamic acid,
wherein the 4-aminobenzoylglutamic acid is not more than 0.1% mole fraction of the composition.

In some embodiments of the compositions provided herein, the composition comprises one or more of 4-aminobenzoylglutamic acid, 10-formylfolic acid, 10-formyldihydrofolic acid, tetrahydropteridine-5-oxide, carboxy-leucguan, hydroxyleucovorin or 7,8-dihydroxanthopterin.

In some embodiments, the composition comprises not more than three of 4-aminobenzoylglutamic acid, folic acid, 10-formylfolic acid, formyltetrahydropteroic acid, diformyltetrahydrofolic acid, 10-formyldihydrofolic acid, 7,8-dihydrofolic acid, methylenetetrahydrofolic acid, tetrahydropteridine-5-oxide, carboxy-leucguan, hydroxyleucovorin or 7,8-dihydroxanthopterin. In some embodiments, the composition comprises 10-formyldihydrofolic acid. In some embodiments, the composition comprises about 0.1% to 0.5% mole fraction of 10-formyldihydrofolic acid. In some embodiments of the compositions provided herein, the 10-formyldihydrofolic acid is not more than about 1% of the mole fraction of the composition. In some embodiments, the 10-formyldihydrofolic acid is not more than about 0.8% mole fraction of the composition. In some embodiments, the 10-formyldihydrofolic acid is not more than about 0.6% mole fraction of the composition. In some embodiments, the 10-formyldihydrofolic acid is not more than about 0.5% mole fraction of the composition. In some embodiments, the 10-formyldihydrofolic acid is not more than about 0.4% mole fraction of the composition. In some embodiments, the 4-aminobenzoylglutamic acid is not more than about 0.1% mole fraction of the composition. In some embodiments, the 4-aminobenzoylglutamic acid is not more than about 0.07% mole fraction of the composition. In some embodiments, the 4-aminobenzoylglutamic acid is not more than about 0.03% mole fraction of the composition.

In some embodiments, the compositions provided herein are pharmaceutical compositions. In some embodiments, the pharmaceutical composition is suitable for injection. In some embodiments, the injectable pharmaceutical composition has a pH of about 7.5 to 8.1.

In some embodiments, the compositions or pharmaceutical compositions provided herein are lyophilized compositions.

In some embodiments, the compositions or pharmaceutical compositions provided herein are aqueous compositions.

In some embodiments, the compositions or pharmaceutical compositions provided herein further comprise 5-fluorouracil.

In some embodiments, the compositions or pharmaceutical compositions provided herein further comprise 5-fluorouracil or a pharmaceutically acceptable salt thereof.

In some embodiments, the compositions or pharmaceutical compositions provided herein comprise an admixture of disodium levoleucovorin and 5-flurouracil or a pharmaceutically acceptable salt thereof, disodium levoleucovorin and methotrexate or a pharmaceutically acceptable salt thereof, disodium levoleucovorin and oxaliplatin or a pharmaceutically acceptable salt thereof, or disodium levoleucovorin and docetaxel or a pharmaceutically acceptable salt thereof.

In some embodiments, the compositions or pharmaceutical compositions provided herein further comprise mannitol. In some embodiments, the concentration of the mannitol in the composition is about 20 to about 40 mg/mL (e.g., about 30 mg/mL).

In some embodiments, the compositions or pharmaceutical compositions provided herein comprise about 50 mg/mL of disodium levoleucovorin, or an amount of disodium levoleucovorin that corresponds to about 50 mg/mL of levofolinic acid.

In some embodiments, the compositions or pharmaceutical compositions provided herein comprise mannitol and disodium levoleucovorin in about a 3:5 w/w ratio, respectively. In some embodiments, the compositions or pharmaceutical compositions provided herein comprise an amount of disodium levoleucovorin such that the composition comprises about a 3:5 w/w ratio of mannitol to levofolinic acid, respectively.

In some embodiments, the compositions provided herein further comprise about 0.9% w/w or mol fraction of sodium chloride. In some embodiments, the compositions provided herein further comprise about 5% w/w or mol fraction of dextrose.

In some embodiments, the compositions provided herein comprise about 175 mg of disodium levoleucovorin (e.g., 140-210 mg of disodium levoleucovorin), or about 300 mg of disodium levoleucovorin (e.g., 240-360 mg of disodium levoleucovorin).

In some embodiments, the compositions provided herein comprise about 105 mg of mannitol (e.g., 84-126 mg of mannitol), or about 180 mg of mannitol (e.g., 144-216 mg of mannitol).

In some embodiments, the compositions provided herein comprise disodium levofolinate and mannitol in amounts about as shown in Table 2.

In some embodiments, the compositions provided herein are more pure, or have improved stability (e.g., improved shelf-stability), than known levofolinate (e.g., disodium levofolinate or calcium levofolinate) compositions. Without being bound by theory, the improvement results from the processes provided herein.

Thus, in some embodiments, the additional components of the compositions provided herein may be considered as impurities. In some embodiments, the total mole fraction of impurities in the composition is about 1.0% or less, about 0.9% or less, about 0.8% or less, about 0.7% or less, about 0.6% or less, about 0.5% or less, about 0.4% or less, about 0.3% or less, or about 0.2% or less. In some embodiments, the total mole fraction of impurities in the composition is about 0.7% or less. In some embodiments, the total mole fraction of impurities in the composition is about 0.5% or less. In some embodiments, the total mole fraction of impurities in the composition is about 0.4% or less.

In some embodiments, the impurities are 4-Aminobenzoylglutamic acid (PABGA), Folic acid (FA), 10-Formylfolic acid (FFA), Formyltetrahydropteroic acid (FTHPA), Diformyltetrahydrofolic acid (DFTHFA), 10-Formyldihydrofolic acid (FDHFA), 7,8-Dihydrofolic acid (DHFA), Methylenetetrahydrofolic acid (CH2-THFA), Tetrahydropteridine-5-Oxide (THP5O), Carboxy-Leucguan (CLG), Hydroxyleucovorin (HL), and 7,8-Dihydroxanthopterin.

In some embodiments, the compositions provided herein have improved stability relative to known levofolinate (e.g., disodium levofolinate or calcium levofolinate) compositions. Thus, in some embodiments, the total mole fraction of impurities increases by about 50% after 6 months of storage. In some embodiments, the total mole fraction of impurities increases by about 40% after 6 months of storage. In some embodiments, the total mole fraction of impurities increases by about 30% after 6 months of storage. In some embodiments, the total mole fraction of impurities increases by about 25% after 6 months of storage. In some embodiments, the total mole fraction of impurities increases by about 20% after 6 months of storage. In some embodiments, the total mole fraction of impurities increases by about 15% after 6 months of storage. In some embodiments, the total mole fraction of impurities increases by about 10% after 6 months of storage. In some embodiments, the total mole fraction of impurities increases by about 5% after 6 months of storage. In some embodiments, the total mole fraction of impurities increases by about 4% after 6 months of storage. In some embodiments, the total mole fraction of impurities increases by about 3% after 6 months of storage. In some embodiments, the total mole fraction of impurities increases by about 2% after 6 months of storage. In some embodiments, the total mole fraction of impurities increases by about 1% after 6 months of storage. In some embodiments, the total mole fraction of impurities increases by not more than the percentages specified above.

Processes

Also described herein are processes to prepare a lyophilized composition including disodium levofolinate. In some embodiments, the process can be accomplished at a temperature of less than about 18° C.

Lyophilized powder is a dosage form intended for injection prepared by lyophilization ("freeze drying"), a process which involves the removal of water from products in the frozen state. A process for the preparation of a lyophilized composition including disodium levofolinate comprises, sparging water with nitrogen and then adding mannitol to the sparged water at a temperature of less than about 18° C. The sparged water and mannitol is then mixed until the mannitol is completely dissolved. Levofolinic acid can then be added to the water and mannitol solution. Aqueous sodium hydroxide can be added to the levofolinic acid mixture to achieve pH of the solution to about 7.8 to about 8.0. The aqueous solution can then be filtered and lyophilized such that the lyophilized composition is prepared under nitrogen atmosphere.

In some embodiments, the process of preparing the disodium levofolinate composition can require that the temperature is maintained at about 15° C. to about 17° C.

In one aspect, provided herein are processes of preparing the lyophilized compositions provided herein, comprising: mixing mannitol and levofolinic acid in sparged water under inert atmosphere; adding aqueous sodium hydroxide to the levofolinic acid and mannitol; filtering the solution; and lyophilizing the filtered solution such that the lyophilized composition is prepared.

In some embodiments, the processes provided herein comprise:
  a) sparging water with nitrogen;
  b) adding mannitol to the sparged water at a temperature of less than about 18° C.;
  c) mixing the mannitol and sparged water until the mannitol is completely dissolved;
  d) adding levofolinic acid to the mannitol solution;
  e) adding aqueous sodium hydroxide to the levofolinic acid and mannitol mixture until pH of the solution is about 7.8 to 8.0;
  f) filtering the levofolinic acid solution; and
  g) lyophilizing the filtered solution such that the lyophilized composition is prepared,
  wherein at least one of the steps of the process is performed under an inert atmosphere.

In some embodiments, steps a, b and c are performed under an inert atmosphere.

In some embodiments, each step of the process is performed under an inert atmosphere.

In some embodiments, the temperature of the mixture is maintained at about 15° C. to 17° C. during steps a) to f).

In some embodiments, the inert atmosphere is a nitrogen or an argon atmosphere. In some embodiments, the inert atmosphere is a nitrogen atmosphere. In some embodiments, the inert atmosphere is an argon atmosphere.

In some embodiments, the pH of the solution is about 7.9.

Methods

In some embodiments, the compositions described herein can be used in the preparation of a medicament for the treatment of cancer, folic acid deficiency or methotrexate toxicity rescue.

In some embodiments, provided herein are methods of treating cancer in a subject in need thereof, comprising administering 5-fluorouracil and a composition (e.g., an aqueous composition, e.g., a pharmaceutical composition) provided herein to the subject. In some embodiments, the cancer is a colorectal cancer.

In some embodiments, the composition and the 5-fluorouracil are administered simultaneously (e.g., in parallel, or as a single composition). In some embodiments, the composition and the 5-fluorouracil are administered separately (e.g., in series).

In some embodiments, provided herein are methods of treating cancer with high-dose methotrexate and reducing the immediate toxic effects of methotrexate in a subject in need thereof, comprising administering a composition (e.g., an aqueous composition, e.g., a pharmaceutical composition) provided herein to the subject. In some embodiments, the cancer is a sarcoma (e.g., an osteosarcoma).

In some embodiments, provided herein are methods of minimizing systemic toxicity from methotrexate overdose in a subject in need thereof, comprising administering a composition (e.g., an aqueous composition, e.g., a pharmaceutical composition) provided herein to the subject.

In some embodiments, provided herein are methods of treating folic acid deficiency in a subject in need thereof, comprising administering a composition (e.g., an aqueous composition, e.g., a pharmaceutical composition) provided herein to the subject.

In some embodiments, provided herein are methods of treating megaloblastic anemia in a subject in need thereof, comprising administering a composition (e.g., an aqueous composition, e.g., a pharmaceutical composition) provided herein to the subject.

In some embodiments, the megaloblastic anemia is due to sprue, nutritional deficiency, pregnancy, infancy, liver disease or malabsorption syndrome.

Thus, in some embodiments of the methods provided herein, the composition is a composition comprising:
 a) disodium levofolinate;
 b) 10-formyldihydrofolic acid; and
 c) 4-aminobenzoylglutamic acid,
 wherein the 10-formyldihydrofolic acid is not more than about 1% of the mole fraction of the composition.

In some embodiments, the composition is a composition comprising:
 a) disodium levofolinate;
 b) 10-formyldihydrofolic acid; and
 c) 4-aminobenzoylglutamic acid,
 wherein the 4-aminobenzoylglutamic acid is not more than about 0.1% mole fraction of the composition.

In some embodiments, the compositions further comprises mannitol, 5-fluorouracil, or both.

In some embodiments provided herein are methods of treating colorectal cancer in a subject in need thereof, comprising administering to the subject 5-fluorouracil and a composition comprising:
 a) disodium levofolinate;
 b) 10-formyldihydrofolic acid; and
 c) 4-aminobenzoylglutamic acid,
 wherein the 10-formyldihydrofolic acid is not more than about 1% of the mole fraction of the composition.

In some embodiments provided herein are methods of treating colorectal cancer in a subject in need thereof, comprising administering to the subject 5-fluorouracil and a composition comprising:
 a) disodium levofolinate;
 b) 10-formyldihydrofolic acid; and
 c) 4-aminobenzoylglutamic acid,
 wherein the 4-aminobenzoylglutamic acid is not more than about 0.1% mole fraction of the composition.

In some embodiments, provided herein are methods of treating a sarcoma with high-dose methotrexate and reducing the immediate toxic effects of the methotrexate in a subject in need thereof, comprising administering to the subject a composition comprising:
 a) disodium levofolinate;
 b) 10-formyldihydrofolic acid; and
 c) 4-aminobenzoylglutamic acid,
 wherein the 10-formyldihydrofolic acid is not more than about 1% of the mole fraction of the composition.

In some embodiments, provided herein are methods of treating a sarcoma with high-dose methotrexate and reducing the immediate toxic effects of the methotrexate in a subject in need thereof, comprising administering to the subject a composition comprising:
 a) disodium levofolinate;
 b) 10-formyldihydrofolic acid; and
 c) 4-aminobenzoylglutamic acid,
 wherein the 4-aminobenzoylglutamic acid is not more than about 0.1% mole fraction of the composition.

In some embodiments, provided herein are methods of minimizing systemic toxicity from methotrexate overdose in a subject in need thereof, comprising administering to the subject a composition comprising:
 a) disodium levofolinate;
 b) 10-formyldihydrofolic acid; and
 c) 4-aminobenzoylglutamic acid,
 wherein the 10-formyldihydrofolic acid is not more than about 1% of the mole fraction of the composition.

In some embodiments, provided herein are methods of minimizing systemic toxicity from methotrexate overdose in a subject in need thereof, comprising administering to the subject a composition comprising:
 a) disodium levofolinate;
 b) 10-formyldihydrofolic acid; and
 c) 4-aminobenzoylglutamic acid,
 wherein the 4-aminobenzoylglutamic acid is not more than about 0.1% mole fraction of the composition.

In some embodiments, provided herein are methods of treating folic acid deficiency in a subject in need thereof, comprising administering to the subject a composition comprising:
 a) disodium levofolinate;
 b) 10-formyldihydrofolic acid; and
 c) 4-aminobenzoylglutamic acid,
 wherein the 10-formyldihydrofolic acid is not more than about 1% of the mole fraction of the composition.

In some embodiments, provided herein are methods of treating folic acid deficiency in a subject in need thereof, comprising administering to the subject a composition comprising:
 a) disodium levofolinate;
 b) 10-formyldihydrofolic acid; and
 c) 4-aminobenzoylglutamic acid,
 wherein the 4-aminobenzoylglutamic acid is not more than about 0.1% mole fraction of the composition.

EXAMPLES

The following Examples further illustrate aspects of the compositions and methods provided herein. However, these Examples are in no way a limitation of the teachings or disclosure as set forth herein. These Examples are provided for illustration purposes.

Example 1: Bulk Drug Solution Formulation

Approximately 80% of the required amount of Water for Injection (WFI) was added to the 45 L glass carboy, the mixer was turned on and sparged with nitrogen. Then the required amounts of mannitol and levofolinic acid were added and dissolved in the WFI. The levofolinic acid was converted to its disodium salt (disodium levofolinate) using 5N sodium hydroxide. The temperature of the bulk solution was kept at around 15-17° C. and the solution pH was adjusted to 7.9 (range: 7.8-8.0). The bulk solution was brought to the final volume (weight) with Water for Injection and pH of the solution was checked again.

Example 2: Aseptic Filtration and Filling

The formulated bulk solution was sterile-filtered and filled into 10 mL vials. The filled vials were partially stoppered and loaded onto cold lyophilizer shelves and lyophilized.

Example 3: Lyophilization and Capping

At the end of lyophilization cycle, the lyophilizer was backfilled with nitrogen, vials completely stoppered and then removed from lyophilizer. The specifics of each formulation are shown below in Table 2 of Example 6.

Example 4: DSC Analysis

DSC analysis was conducted on the sample containing no mannitol, and on the sample containing mannitol to determine the glass transition and or eutectic melting temperatures, and to determine if mannitol made a difference. Using a pipette, a 15 μL aliquot of the liquid was pipetted into an aluminum DSC sample pan and hermetically sealed.

Figure 2:
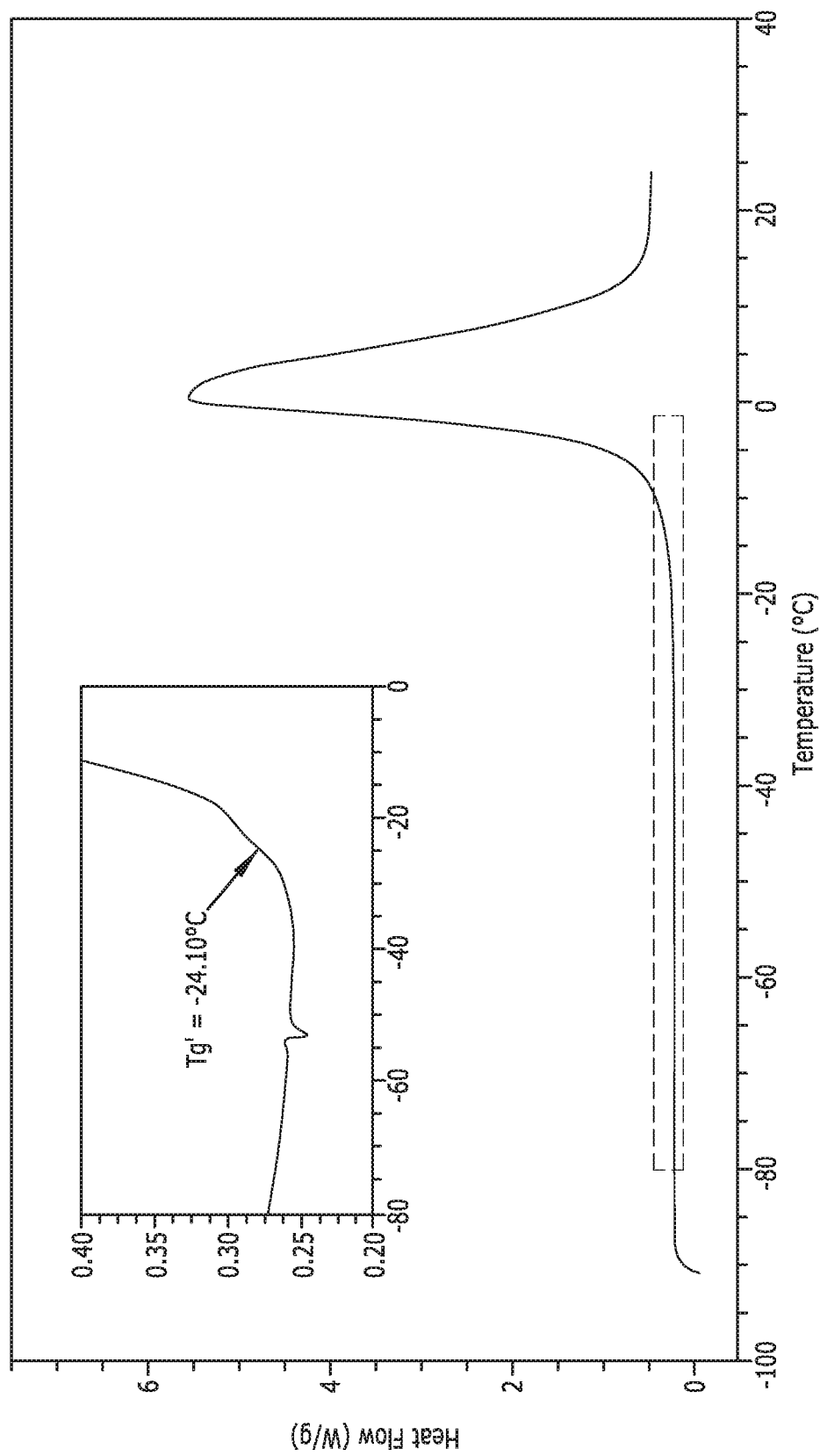
FIG. 2 illustrates a DSC thermogram of disodium levofolinate and 10 mg/mL mannitol showing a glass transition occurring at −24.10° C.

The method used for the sample was as follows: the sample and reference pan (an empty aluminum pan) were loaded into the DSC at 40° C. and were then cooled to −90° C. at 10° C./minute and held there for 2 minutes. The sample was then warmed to 30° C. at 10° C./minute. The results from the DSC analysis are shown in FIG. 1 and FIG. 2.

Example 5: HPLC Method a. Solutions
  i. Tetrabutylammonium phosphate (TBA-$PO_4$) in MeOH, 1.0M.
  ii. Mobile Phase A (MPA)—10 mM $Na_2PO_4$, 50 mM TBA-$PO_4$ in water.
  iii. Mobile Phase B (MPB)—100% MeOH
  iv. Diluent (0.005N NaOH). This solution was stored in the refrigerator at 2-8° C.
b. Standard: USP Leucovorin Calcium was used as a reference standard.
  i. Standard Preparation for Assay—0. 9 mg/mL
  ii. Resolution Solution—4.6 mg Leucovorin Calcium reference standard, 2.7 mg FFA, 2.0 mg 4-Aminobenzoylglutamic acid (PABGA), and 3.5 mg 10-Formyldihydrofolic acid (FDHFA) was weighed and transferred to 50 mL volumetric flask. Purified water was added, and the flask was swirled until all solids dissolved. Then the solution was brought to volume with purified water and mixed.

c. Sample preparation
  i. Bulk drug substance (BDS)— 48.9 mg of LFA was weighed and transferred to a 50 mL volumetric flask. Diluent was added and the flask was swirled until the solids dissolved. Then the solution was brought to volume with diluent and mixed.
  ii. Lyophilized Sample Preparation—Each vial was reconstituted with about 5 mL of diluent. The contents were withdrawn and transferred to a 25 mL volumetric flask. The vial was then rinsed with 4 successive 3 mL aliquots of diluent, which were transferred to the same 25 mL flask. The flask was brought to volume with diluent, and mixed. 3.5 mL of this solution was transferred to another 25 mL volumetric flask. The flask was brought to volume with diluent, mixed, and analyzed.
d. HPLC analysis
The system was set up according to the provided HPLC method (Table 1): Flow rate=1.0 mL/min; Column temperature=30° C.; Sampler temperature=5° C.; Injection volume=10 μL; Detection wavelength=54 nm; Bandwidth=12 nm; Reference wavelength=360 nm; Reference bandwidth=100 nm.

TABLE 1

HPLC Gradient

| Time (min) | % A | % B |
|---|---|---|
| 0 | 85 | 15 |
| 30 | 76 | 24 |
| 38 | 76 | 24 |
| 38.10 | 85 | 15 |
| 52 | 85 | 15 |

Example 6: Stability Studies of Disodium Levofolinate Drug Product for Injection Tables 3-19 summarize the results of the various stability studies conducted (ND indicates "not detected"). Samples (Table 2) were analyzed by HPLC according to Example 5.

TABLE 2

Summary of Materials

| Batch # | Strength (disodium levofolinate) | Mannitol |
|---|---|---|
| 1 | 50 mg/vial | 30 mg/mL |
| 2 | 50 mg/vial | 30 mg/mL |
| 3 | 175 mg/vial | 30 mg/mL |
| 4 | 300 mg/vial | 30 mg/mL |
| 5 | 300 mg/mL | 30 mg/mL |
| 6 | 50 mg/vial | 10 mg/vial |
| 7 | 50 mg/vial | none |
| 8 | 300 mg/vial | none |
| 9 | 175 mg/vial | 35 mg/vial |
| 10 | 300 mg/vial | 60 mg/vial |
| 11 | 300 mg/vial | 180 mg/vial |
| 12 | 50 mg/mL | 10 mg/mL |
| 13 | 50 mg/mL | None |
| 14 | 50 mg/mL | 30 mg/mL |
| 15 | 175 mg/vial | 105 mg/vial |

Stability of batch #1 and batch #2 were monitored by HPLC. 10-Formyldihydrofolic acid (FDHFA) is the only impurity >0.1%. This impurity showed a highest level of about 0.5% mol fraction at 2 months at 25 C/60% RH and 40 C/75% RH. This impurity stayed below ~0.5% level for all conditions tested up to 3 months. Until 3 months, this impurity (10-Formyldihydrofolic acid stayed well below specification limit (NMT 1.3).

Stability of batch #3 and batch #4 were monitored by HPLC. 10-Formyldihydrofolic acid (FDHFA) was the only impurity >0.1% at TO.

These data indicate that no particular trend for the presence of the main impurity [10-Formyldihydrofolic acid (FDHFA)]. 10-Formyldihydrofolic acid (FDHFA) remained below specification (NMT 1.3).

TABLE 3

Stability of Batch #1 (lyo) at 5° C.

|  | Test | | | | |
| --- | --- | --- | --- | --- | --- |
|  | Initial | 2 mo | 6 mo | 12 mo | 18 mo |
| Assay | 100.5 | 95.1 | 100.0 | 99.3 | 98.9 |
| Total Impurities | 0.46 | 0.46 | 0.49 | 0.49 | 0.54 |
| Specified impurities | | | | | |
| 4-Aminobenzoylglutamic acid (PABGA) | ND | ND | ND | ND | 0.02 |
| Folic acid (FA) | ND | ND | ND | ND | ND |
| 10-Formylfolic acid (FFA) | ND | ND | ND | ND | ND |

TABLE 3-continued

Stability of Batch #1 (lyo) at 5° C.

|  | Test | | | | |
| --- | --- | --- | --- | --- | --- |
|  | Initial | 2 mo | 6 mo | 12 mo | 18 mo |
| Formyltetrahydropteroic acid (FTHPA) | ND | ND | ND | ND | ND |
| Diformyltetrahydrofolic acid (DFTHFA) | ND | ND | ND | ND | ND |
| 10-Formyldihydrofolic acid (FDHFA) | 0.46 | 0.46 | 0.49 | 0.49 | 0.52 |
| 7,8-Dihydrofolic acid (DHFA) | ND | ND | ND | ND | ND |
| Methylenetetrahydrofolic acid (CH2-THFA) | ND | ND | ND | ND | ND |
| Tetrahydropteridine-5-Oxide (THP5O) | ND | ND | ND | ND | ND |
| Carboxy-Leucguan (CLG) | ND | ND | ND | ND | ND |
| Hydroxyleucovorin (HL) | ND | ND | ND | ND | ND |
| 7,8-Dihydroxanthopterin | ND | ND | ND | ND | ND |
| Other individual unspecified related substances | ND | ND | ND | ND | ND |

TABLE 4

Stability of Batch# 1 (lyo) at 25° C./60%RH

|  | Test | | | | | | |
| --- | --- | --- | --- | --- | --- | --- | --- |
|  | Initial | 2 mo | 3 mo | 6 mo | 12 mo | 18 mo | 24 mo |
| Assay | 100.5 | 99.8 | 100.3 | 99.1 | 99.2 | 99.2 | 98.8 |
| Total Impurities | 0.46 | 0.52 | 0.49 | 0.51 | 0.51 | 0.91 | 0.57 |
| Specified impurities | | | | | | | |
| 4-Aminobenzoylglutamic acid (PABGA) | ND | ND | ND | ND | ND | 0.06 | 0.04 |
| Folic acid (FA) | ND | ND | ND | ND | ND | ND | ND |
| 10-Formylfolic acid (FFA) | ND | ND | ND | ND | ND | 0.03 | ND |
| Formyltetrahydropteroic acid (FTHPA) | ND | ND | ND | ND | ND | ND | ND |
| Diformyltetrahydrofolic acid (DFTHFA) | ND | ND | ND | ND | ND | ND | ND |
| 10-Formyldihydrofolic acid (FDHFA) | 0.46 | 0.52 | 0.49 | 0.51 | 0.51 | 0.54 | 0.53 |
| 7,8-Dihydrofolic acid (DHFA) | ND | ND | ND | ND | ND | ND | ND |
| Methylenetetrahydrofolic acid (CH2-THFA) | ND | ND | ND | ND | ND | ND | ND |
| Tetrahydropteridine-5-Oxide (THP5O) | ND | ND | ND | ND | ND | 0.10 | ND |
| Carboxy-Leucguan (CLG) | ND | ND | ND | ND | ND | ND | ND |
| Hydroxyleucovorin (HL) | ND | ND | ND | ND | ND | ND | ND |
| 7,8-Dihydroxanthopterin | ND | ND | ND | ND | ND | ND | ND |
| individual unspecified related substances | ND | ND | ND | ND | ND | 0.18 | ND |

TABLE 5

Stability of Batch# 1 (lyo) at 40° C./75%RH

|  | Test | | | | | |
| --- | --- | --- | --- | --- | --- | --- |
|  | Initial | 1 mo | 2 mo | 3 mo | 6 mo | 18 mo |
| Assay | 100.5 | 95.1 | 98.4 | 98.8 | 93.5 | 99.3 |
| Total Impurities | 0.46 | 0.34 | 0.50 | 0.49 | 0.52 | 1.00 |
| Specified impurities | | | | | | |
| 4-Aminobenzoylglutamic acid (PABGA) | ND | ND | ND | ND | ND | 0.06 |
| Folic acid (FA) | ND | ND | ND | ND | ND | ND |
| 10-Formylfolic acid (FFA) | ND | ND | ND | ND | ND | 0.07 |

TABLE 5-continued

Stability of Batch# 1 (lyo) at 40° C./75%RH

| | Test | | | | | |
|---|---|---|---|---|---|---|
| | Initial | 1 mo | 2 mo | 3 mo | 6 mo | 18 mo |
| Formyltetrahydropteroic acid (FTHPA) | ND | ND | ND | ND | ND | ND |
| Diformyltetrahydrofolic acid (DFTHFA) | ND | ND | ND | ND | ND | ND |
| 10-Formyldihydrofolic acid (FDHFA) | 0.46 | 0.34 | 0.50 | 0.49 | 0.52 | 0.60 |
| 7,8-Dihydrofolic acid (DHFA) | ND | ND | ND | ND | ND | ND |
| Methylenetetrahydrofolic acid (CH2-THFA) | ND | ND | ND | ND | ND | ND |
| Tetrahydropteridine-5-Oxide (THP5O) | ND | ND | ND | ND | ND | 0.15 |
| Carboxy-Leucguan (CLG) | ND | ND | ND | ND | ND | ND |
| Hydroxyleucovorin (HL) | ND | ND | ND | ND | ND | ND |
| 7,8-Dihydroxanthopterin | ND | ND | ND | ND | ND | ND |
| Other individual unspecified related substances | ND | ND | ND | ND | ND | 0.12 |

TABLE 6

Stability data of Batch #2 (lyo) at 5° C.

| | Test | | | |
|---|---|---|---|---|
| | Initial | 2 mo | 6 mo | 12 mo |
| Assay | 100.8 | 100.0 | 99.9 | 99.9 |
| Total Impurities | 0.48 | 0.49 | 0.48 | 0.49 |
| Specified impurities | | | | |
| 4-Aminobenzoylglutamic acid (ABGA) | ND | ND | ND | ND |
| Folic acid (FA) | ND | ND | ND | ND |
| 10-Formylfolic acid (FFA) | ND | ND | ND | ND |
| Formyltetrahydropteroic acid (FTHPA) | ND | ND | ND | ND |
| Diformyltetrahydrofolic acid (DFTHFA) | ND | ND | ND | ND |
| 10-Formyldihydrofolic acid (FDHFA) | 0.48 | 0.49 | 0.49 | 0.49 |
| 7,8-Dihydrofolic acid (DHFA) | ND | ND | ND | ND |
| Methylenetetrahydrofolic acid (CH2-THFA) | ND | ND | ND | ND |
| Tetrahydropteridine-5-Oxide (THP5O) | ND | ND | ND | ND |
| Carboxy-Leucguan (CLG) | ND | ND | ND | ND |
| Hydroxyleucovorin (HL) | ND | ND | ND | ND |
| 7,8-Dihydroxanthopterin | ND | ND | ND | ND |
| Individual unspecified related substances | ND | ND | ND | ND |

TABLE 7

Stability data of Batch# 2 (lyo) at 25° C./60%RH

| | Test | | | | | | |
|---|---|---|---|---|---|---|---|
| | Initial | 2 mo | 3 mo | 6 mo | 12 mo | 18 mo | 24 mo |
| Assay | 100.8 | 100.4 | 98.2 | 99.5 | 99.5 | 98.1 | 99.9 |
| Total Impurities | 0.48 | 0.49 | 0.47 | 0.51 | 0.51 | 0.79 | 0.62 |
| Specified impurities | | | | | | | |
| 4-Aminobenzoylglutamic acid (ABGA) | ND | ND | 0.02 | ND | ND | 0.05 | 0.04 |
| Folic acid (FA) | ND | ND | ND | ND | ND | ND | ND |
| 10-Formylfolic acid (FFA) | ND | ND | ND | ND | ND | 0.03 | ND |
| Formyltetrahydropteroic acid (FTHPA) | ND | ND | ND | ND | ND | ND | ND |
| Diformyltetrahydrofolic acid (DFTH FA) | ND | ND | ND | ND | ND | ND | ND |
| 10-Formyldihydrofolic acid (FDHFA) | 0.48 | 0.49 | 0.45 | 0.51 | 0.51 | 0.56 | 0.58 |
| 7,8-Dihydrofolic acid (DHFA) | ND | ND | ND | ND | ND | ND | ND |
| Methylenetetrahydrofolic acid (CH2-THFA) | ND | ND | ND | ND | ND | ND | ND |
| Tetrahydropteridine-5-Oxide (THP5O) | ND | ND | ND | ND | ND | 0.07 | ND |

TABLE 7-continued

Stability data of Batch# 2 (lyo) at 25° C./60%RH

| | Test | | | | | | |
|---|---|---|---|---|---|---|---|
| | Initial | 2 mo | 3 mo | 6 mo | 12 mo | 18 mo | 24 mo |
| Carboxy-Leucguan (CLG) | ND | ND | ND | ND | ND | ND | ND |
| Hydroxyleucovorin (HL) | ND | ND | ND | ND | ND | ND | ND |
| 7,8-Dihydroxanthopterin | ND | ND | ND | ND | ND | ND | ND |
| individual unspecified related substances | ND | ND | ND | ND | ND | 0.11 | ND |

TABLE 8

Stability data of Batch #2 (lyo) at 40° C./75%RH

| | Test | | | | |
|---|---|---|---|---|---|
| | Initial | 1 mo | 2 mo | 3 mo | 6 mo |
| Assay | 100.8 | 100.4 | 100.7 | 100.2 | 100.1 |
| Total Impurities | 0.48 | 0.31 | 0.52 | 0.34 | 0.56 |
| Specified impurities | | | | | |
| 4-Aminobenzoylglutamic acid (ABGA) | ND | ND | ND | ND | ND |
| Folic acid (FA) | ND | ND | ND | ND | ND |
| 10-Formylfolic acid (FFA) | ND | ND | ND | ND | ND |
| Formyltetrahydropteroic acid (FTHPA) | ND | ND | ND | ND | ND |
| Diformyltetrahydrofolic acid (DFTHFA) | ND | ND | ND | ND | ND |
| 10-Formyldihydrofolic acid (FDHFA) | 0.48 | 0.31 | 0.52 | 0.34 | 0.56 |
| 7,8-Dihydrofolic acid (DHFA) | ND | ND | ND | ND | ND |
| Methylenetetrahydrofolic acid (CH2-THFA) | ND | ND | ND | ND | ND |
| Tetrahydropteridine-5-Oxide (THP5O) | ND | ND | ND | ND | ND |
| Carboxy-Leucguan (CLG) | ND | ND | ND | ND | ND |
| Hydroxyleucovorin (HL) | ND | ND | ND | ND | ND |
| 7,8-Dihydroxanthopterin | ND | ND | ND | ND | ND |
| Individual unspecified related substances | ND | ND | ND | ND | ND |

TABLE 9

Stability data of Batch #3 (lyo) at 5° C.

| | Test | | | |
|---|---|---|---|---|
| | Initial | 3 mo | 6 mo | 12 mo |
| Assay | 98.5 | 97.9 | 99.0 | 99.1 |
| Total Impurities | 0.44 | 0.48 | 0.53 | 0.41 |
| Specified impurities | | | | |
| 4-Aminobenzoylglutamic acid (ABGA) | ND | ND | ND | ND |
| Folic acid (FA) | ND | ND | ND | ND |
| 10-Formylfolic acid (FFA) | ND | ND | ND | ND |
| Formyltetrahydropteroic acid (FTHPA) | ND | ND | ND | ND |
| Diformyltetrahydrofolic acid (DFTHFA) | ND | ND | ND | ND |
| 10-Formyldihydrofolic acid (FDHFA) | 0.44 | 0.48 | 0.53 | 0.41 |
| 7,8-Dihydrofolic acid (DHFA) | ND | ND | ND | ND |
| Methylenetetrahydrofolic acid (CH2-THFA) | ND | ND | ND | ND |
| Tetrahydropteridine-5-Oxide (THP5O) | ND | ND | ND | ND |
| Carboxy-Leucguan (CLG) | ND | ND | ND | ND |
| Hydroxyleucovorin (HL) | ND | ND | ND | ND |
| 7,8-Dihydroxanthopterin | ND | ND | ND | ND |
| Individual unspecified related substances | ND | ND | ND | ND |

TABLE 10

Stability data of Batch# 3 (lyo) at 25° C./60%RH

| | Test | | | | | |
|---|---|---|---|---|---|---|
| | Initial | 3 mo | 6 mo | 12 mo | 18 mo | 24 mo |
| Assay | 98.5 | 97.8 | 97.8 | 97.9 | 97.8 | 97.3 |
| Total Impurities | 0.44 | 0.48 | 0.52 | 0.44 | 0.41 | 0.51 |
| Specified impurities | | | | | | |
| 4-Aminobenzoylglutamic acid (ABGA) | ND | ND | ND | ND | ND | 0.05 |
| Folic acid (FA) | ND | ND | ND | ND | ND | ND |
| 10-Formylfolic acid (FFA) | ND | ND | ND | ND | ND | ND |
| Formyltetrahydropteroic acid (FTHPA) | ND | ND | ND | ND | ND | ND |
| Diformyltetrahydrofolic acid (DFTHFA) | ND | ND | ND | ND | ND | ND |
| 10-Formyldihydrofolic acid (FDHFA) | 0.44 | 0.48 | 0.52 | 0.44 | 0.41 | 0.46 |
| 7,8-Dihydrofolic acid (DHFA) | ND | ND | ND | ND | ND | ND |
| Methylenetetrahydrofolic acid (CH2-THFA) | ND | ND | ND | ND | ND | ND |
| Tetrahydropteridine-5-Oxide (THP5O) | ND | ND | ND | ND | ND | ND |
| Carboxy-Leucguan (CLG) | ND | ND | ND | ND | ND | ND |
| Hydroxyleucovorin (HL) | ND | ND | ND | ND | ND | ND |

TABLE 10-continued

Stability data of Batch# 3 (lyo) at 25° C./60%RH

| | Test | | | | | |
|---|---|---|---|---|---|---|
| | Initial | 3 mo | 6 mo | 12 mo | 18 mo | 24 mo |
| 7,8-Dihydroxanthopterin | ND | ND | ND | ND | ND | ND |
| Individual unspecified related substances | ND | ND | ND | ND | ND | ND |

TABLE 11

Stability data of Batch #3 (lyo) at 40° C./75%RH

| | Test | | | | |
|---|---|---|---|---|---|
| | Initial | 1 mo | 2 mo | 3 mo | 6 mo |
| Assay | 98.5 | 97.6 | 96.7 | 97.2 | 97.8 |
| Total Impurities | 0.44 | 0.44 | 0.40 | 0.50 | 0.53 |
| Specified impurities | | | | | |
| 4-Aminobenzoylglutamic acid (ABGA) | ND | ND | ND | ND | ND |
| Folic acid (FA) | ND | ND | ND | ND | ND |
| 10-Formylfolic acid (FFA) | ND | ND | ND | ND | ND |
| Formyltetrahydropteroic acid (FTHPA) | ND | ND | ND | ND | ND |
| Diformyltetrahydrofolic acid (DFTHFA) | ND | ND | ND | ND | ND |
| 10-Formyldihydrofolic acid (FDHFA) | 0.44 | 0.44 | 0.40 | 0.50 | 0.53 |
| 7,8-Dihydrofolic acid (DHFA) | ND | ND | ND | ND | ND |
| Methylenetetrahydrofolic acid (CH2-THFA) | ND | ND | ND | ND | ND |
| Tetrahydropteridine-5-Oxide (THP5O) | ND | ND | ND | ND | ND |
| Carboxy-Leucguan (CLG) | ND | ND | ND | ND | ND |
| Hydroxyleucovorin (HL) | ND | ND | ND | ND | ND |
| 7,8-Dihydroxanthopterin | ND | ND | ND | ND | ND |
| Individual unspecified related substances | ND | ND | ND | ND | ND |

TABLE 12

Stability data of Batch #4 (lyo) at 5° C.

| | Test | | | |
|---|---|---|---|---|
| | Initial | 3 mo | 6 mo | 12 mo |
| Assay | 101.7 | 99.0 | 100.1 | 98.1 |
| Total Impurities | 0.45 | 0.46 | 0.34 | 0.42 |
| Specified impurities | | | | |
| 4-Aminobenzoylglutamic acid (ABGA) | ND | ND | ND | ND |
| Folic acid (FA) | ND | ND | ND | ND |
| 10-Formylfolic acid (FFA) | ND | ND | ND | ND |
| Formyltetrahydropteroic acid (FTHPA) | ND | ND | ND | ND |
| Diformyltetrahydrofolic acid (DFTHFA) | ND | ND | ND | ND |
| 10-Formyldihydrofolic acid (FDHFA) | 0.38 | 0.46 | 0.34 | 0.42 |
| 7,8-Dihydrofolic acid (DHFA) | ND | ND | ND | ND |
| Methylenetetrahydrofolic acid (CH2-THFA) | ND | ND | ND | ND |
| Tetrahydropteridine-5-Oxide (THP5O) | ND | ND | ND | ND |
| Carboxy-Leucguan (CLG) | ND | ND | ND | ND |
| Hydroxyleucovorin (HL) | ND | ND | ND | ND |
| 7,8-Dihydroxanthopterin | ND | ND | ND | ND |
| Individual unspecified related substances | 0.07 | ND | ND | ND |

TABLE 13

Stability data of Batch# 4 (lyo) at 25° C./60%RH

| | Test | | | | | |
|---|---|---|---|---|---|---|
| | Initial | 3 mo | 6 mo | 12 mo | 18 mo | 24 mo |
| Assay | 101.7 | 98.4 | 99.2 | 98.8 | 98.8 | 98.9 |
| Total Impurities | 0.45 | 0.47 | 0.41 | 0.46 | 0.44 | 0.50 |
| Specified impurities | | | | | | |
| 4-Aminobenzoylglutamic acid (ABGA) | ND | ND | ND | ND | ND | 0.05 |
| Folic acid (FA) | ND | ND | ND | ND | ND | ND |
| 10-Formylfolic acid (FFA) | ND | ND | ND | ND | ND | ND |
| Formyltetrahydropteroic acid (FTHPA) | ND | ND | ND | ND | ND | ND |
| Diformyltetrahydrofolic acid (DFTHFA) | ND | ND | ND | ND | ND | ND |
| 10-Formyldihydrofolic acid (FDHFA) | 0.38 | 0.47 | 0.41 | 0.46 | 0.44 | 0.45 |
| 7,8-Dihydrofolic acid (DHFA) | ND | ND | ND | ND | ND | ND |
| Methylenetetrahydrofolic acid (CH2-THFA) | ND | ND | ND | ND | ND | ND |
| Tetrahydropteridine-5-Oxide (THP5O) | ND | ND | ND | ND | ND | ND |
| Carboxy-Leucguan (CLG) | ND | ND | ND | ND | ND | ND |
| Hydroxyleucovorin (HL) | ND | ND | ND | ND | ND | ND |

TABLE 13-continued

Stability data of Batch# 4 (lyo) at 25° C./60%RH

| Test | Initial | 3 mo | 6 mo | 12 mo | 18 mo | 24 mo |
|---|---|---|---|---|---|---|
| 7,8-Dihydroxanthopterin | ND | ND | ND | ND | ND | ND |
| Individual unspecified related substances | 0.07 | ND | ND | ND | ND | ND |

TABLE 14

Stability data of Batch #4 (lyo) at 40° C./75%RH

| Test | Initial | 1 mo | 2 mo | 6 mo |
|---|---|---|---|---|
| Assay | 101.7 | 98.6 | 95.5 | 98.5 |
| Total Impurities | 0.45 | 0.47 | 0.42 | 0.38 |
| Specified impurities | | | | |
| 4-Aminobenzoylglutamic acid (ABGA) | ND | ND | ND | ND |
| Folic acid (FA) | ND | ND | ND | ND |
| 10-Formylfolic acid (FFA) | ND | ND | ND | ND |
| Formyltetrahydropteroic acid (FTHPA) | ND | ND | ND | ND |
| Diformyltetrahydrofolic acid (DFTHFA) | ND | ND | ND | ND |
| 10-Formyldihydrofolic acid (FDHFA) | 0.38 | 0.47 | 0.42 | 0.38 |
| 7,8-Dihydrofolic acid (DHFA) | ND | ND | ND | ND |
| Methylenetetrahydrofolic acid (CH2-THFA) | ND | ND | ND | ND |
| Tetrahydropteridine-5-Oxide (THP5O) | ND | ND | ND | ND |
| Carboxy-Leucguan (CLG) | ND | ND | ND | ND |
| Hydroxyleucovorin (HL) | ND | ND | ND | ND |
| 7,8-Dihydroxanthopterin | ND | ND | ND | ND |
| Individual unspecified related substances | 0.07 | ND | ND | ND |

TABLE 15

Stability data of Batch# 4 (lyo) 45 hrs at 25° C./60%RH

| Test | Initial | 3 mo | 6 mo | 12 mo | 18 mo | 24 mo |
|---|---|---|---|---|---|---|
| Assay | 101.4 | 98.3 | 99.5 | 96.6 | 98.7 | 98.3 |
| Total Impurities | 0.46 | 0.48 | 0.48 | 0.49 | 0.49 | 0.59 |
| Specified impurities | | | | | | |
| 4-Aminobenzoylglutamic acid (ABGA) | ND | ND | ND | ND | ND | ND |
| Folic acid (FA) | ND | ND | ND | ND | ND | ND |
| 10-Formylfolic acid (FFA) | ND | ND | ND | ND | ND | ND |
| Formyltetrahydropteroic acid (FTHPA) | ND | ND | ND | ND | ND | ND |
| Diformyltetrahydrofolic acid (DFTHFA) | ND | ND | ND | ND | ND | ND |
| 10-Formyldihydrofolic acid (FDHFA) | 0.39 | 0.48 | 0.48 | 0.49 | 0.49 | 0.50 |
| 7,8-Dihydrofolic acid (DHFA) | ND | ND | ND | ND | ND | ND |
| Methylenetetrahydrofolic acid (CH2-THFA) | ND | ND | ND | ND | ND | ND |
| Tetrahydropteridine-5-Oxide (THP5O) | ND | ND | ND | ND | ND | ND |
| Carboxy-Leucguan (CLG) | ND | ND | ND | ND | ND | ND |
| Hydroxyleucovorin (HL) | ND | ND | ND | ND | ND | ND |
| 7,8-Dihydroxanthopterin RRT | ND | ND | ND | ND | ND | ND |
| Individual unspecified related substances | 0.07 | ND | ND | ND | ND | ND |

TABLE 16

Stability data of Batch# 4 (lyo) 53 hrs at 25° C./60%RH

| | Test | | | | | | |
|---|---|---|---|---|---|---|---|
| | Initial | 1 mo | 3 mo | 6 mo | 12 mo | 18 mo | 24 mo |
| Assay | 100.9 | 99.52 | 98.4 | 101.0 | 98.0 | 96.9 | 98.4 |
| Total Impurities | 0.46 | 0.50 | 0.41 | 0.42 | 0.50 | 0.47 | 0.51 |
| Specified impurities | | | | | | | |
| 4-Aminobenzoylglutamic acid (ABGA) | ND | ND | ND | ND | ND | ND | ND |
| Folic acid (FA) | ND | ND | ND | ND | ND | ND | ND |
| 10-Formylfolic acid (FFA) | ND | ND | ND | ND | ND | ND | ND |
| Formyltetrahydropteroic acid (FTHPA) | ND | ND | ND | ND | ND | ND | ND |
| Diformyltetrahydrofolic acid (DFTHFA) | ND | ND | ND | ND | ND | ND | ND |
| 10-Formyldihydrofolic acid (FDHFA) | 0.36 | 0.50 | 0.41 | 0.42 | 0.50 | 0.47 | 0.47 |
| 7,8-Dihydrofolic acid (DHFA) | ND | ND | ND | ND | ND | ND | ND |
| Methylenetetrahydrofolic acid (CH2-THFA) | ND | ND | ND | ND | ND | ND | ND |
| Tetrahydropteridine-5-Oxide (THP5O) | ND | ND | ND | ND | ND | ND | ND |
| Carboxy-Leucguan (CLG) | ND | ND | ND | ND | ND | ND | ND |
| Hydroxyleucovorin (HL) | ND | ND | ND | ND | ND | ND | ND |
| 7,8-Dihydroxanthopterin | ND | ND | ND | ND | ND | ND | ND |
| Individual unspecified related substances | 0.10 | ND | ND | ND | ND | ND | ND |

TABLE 17

Stability data of Batch #5 (lyo) at 5° C.

| | Test | | | |
|---|---|---|---|---|
| | Initial | 2 mo | 3 mo | 12 mo |
| Assay | 97.4 | 99.5 | 98.3 | 99.4 |
| Total Impurities | 0.53 | 0.51 | 0.43 | 0.62 |
| Specified impurities | | | | |
| 4-Aminobenzoylglutamic acid (ABGA) | ND | ND | ND | ND |
| Folic acid (FA) | ND | ND | ND | ND |
| 10-Formylfolic acid (FFA) | ND | ND | ND | ND |
| Formyltetrahydropteroic acid (FTHPA) | ND | ND | ND | ND |
| Diformyltetrahydrofolic acid (DFTHFA) | ND | ND | ND | ND |
| 10-Formyldihydrofolic acid (FDHFA) | 0.53 | 0.51 | 0.43 | 0.62 |
| 7,8-Dihydrofolic acid (DHFA) | ND | ND | ND | ND |
| Methylenetetrahydrofolic acid (CH2-THFA) | ND | ND | ND | ND |
| Tetrahydropteridine-5-Oxide (THP5O) | ND | ND | ND | ND |
| Carboxy-Leucguan (CLG) | ND | ND | ND | ND |
| Hydroxyleucovorin (HL) | ND | ND | ND | ND |
| 7,8-Dihydroxanthopterin | ND | ND | ND | ND |
| Individual unspecified related substances | ND | ND | ND | ND |

TABLE 18

Stability data of Batch #5 (lyo) at 25° C./60%RH

| | Test | | | | |
|---|---|---|---|---|---|
| | Initial | 2 mo | 3 mo | 9 mo | 12 mo |
| Assay | 97.4 | 98.3 | 98.5 | 99.4 | 99.2 |
| Total Impurities | 0.53 | 0.50 | 0.45 | 0.44 | 0.78 |
| Specified impurities | | | | | |
| 4-Aminobenzoylglutamic acid (ABGA) | ND | ND | ND | 0.03 | 0.07 |
| Folic acid (FA) | ND | ND | ND | ND | ND |
| 10-Formylfolic acid (FFA) | ND | ND | ND | ND | ND |
| Formyltetrahydropteroic acid (FTHPA) | ND | ND | ND | ND | ND |
| Diformyltetrahydrofolic acid (DFTHFA) | ND | ND | ND | ND | ND |
| 10-Formyldihydrofolic acid (FDHFA) | 0.53 | 0.50 | 0.45 | 0.41 | 0.61 |
| 7,8-Dihydrofolic acid (DHFA) | ND | ND | ND | ND | ND |
| Methylenetetrahydrofolic acid (CH2-THFA) | ND | ND | ND | ND | ND |
| Tetrahydropteridine-5-Oxide (THP5O) | ND | ND | ND | ND | ND |
| Carboxy-Leucguan (CLG) | ND | ND | ND | ND | ND |
| Hydroxyleucovorin (HL) | ND | ND | ND | ND | ND |
| 7,8- Dihydroxanthopterin RRT ≈ 0.12/0.13 | ND | ND | ND | ND | ND |
| Individual unspecified related substances | ND | ND | ND | ND | 0.10 |

TABLE 19

Stability data of Batch #5 (lyo) at 40° C./75%RH

| | Test | | | | |
|---|---|---|---|---|---|
| | Initial | 2 mo | 3 mo | 9 mo | 12 mo |
| Assay | 97.4 | 99.3 | 99.2 | 99.2 | 99.3 |
| Total Impurities | 0.53 | 0.52 | 0.46 | 0.49 | 0.75 |
| Specified impurities | | | | | |
| 4-Aminobenzoylglutamic acid (ABGA) | ND | ND | ND | 0.04 | 0.07 |
| Folic acid (FA) | ND | ND | ND | ND | ND |
| 10-Formylfolic acid (FFA) | ND | ND | ND | ND | ND |
| Formyltetrahydropteroic acid (FTHPA) | ND | ND | ND | ND | ND |
| Diformyltetrahydrofolic acid (DFTHFA) | ND | ND | ND | ND | ND |
| 10-Formyldihydrofolic acid (FDHFA) | 0.53 | 0.52 | 0.46 | 0.43 | 0.64 |
| 7,8-Dihydrofolic acid (DHFA) | ND | ND | ND | ND | ND |
| Methylenetetrahydrofolic acid (CH2-THFA) | ND | ND | ND | ND | ND |
| Tetrahydropteridine-5-Oxide (THP5O) | ND | ND | ND | 0.02 | 0.04 |
| Carboxy-Leucguan (CLG) | ND | ND | ND | ND | ND |
| Hydroxyleucovorin (HL) | ND | ND | ND | ND | ND |
| 7,8-Dihydroxanthopterin RRT ≈ 0.12/0.13 | ND | ND | ND | ND | ND |
| Individual unspecified related substances | ND | ND | ND | ND | ND |

Certain additional compositions are shown in Table 20.

TABLE 20

Comparison of Certain Formulation Compositions comprising Disodium Levoleucovorin.

| | Disodium Levoleucovorin for Injection (175 mg/vial) | | Disodium Levoleucovorin for Injection (300 mg/vial) | |
|---|---|---|---|---|
| Components | Qty. per vial (mg) | % w/w | Qty. per vial (mg) | % w/w |
| Levofolinic acid | 190.0 | 56.3 | 322.5 | 56.3 |
| Mannitol | 114.0 | 33.8 | 193.5 | 33.8 |
| Sodium Hydroxide (approximate amount) | to adjust pH (~33.3) | 9.9 | to adjust pH (~56.4) | 9.9 |
| Hydrochloric acid | q.s. to adjust pH | N/A | q.s. to adjust pH | N/A |

Example 7: Chemical Compatibility

A chemical compatibility study utilized both 175 mg/vial and 300 mg/vial strength products for stability evaluation over 24 hours with sampling at initial, 6 hours, and 24 hours. Drug product vials were reconstituted with 0.9% saline at 50 mg/mL concentration and kept at 20-25° C. throughout. Samples were tested against pre-set specifications that matched the quality specification in place for the commercial drug product. All the test results obtained with reconstituted Disodium Levoleucovorin Drug Product samples were well within specifications throughout the 24-hour study. Drug Assay, Impurity, Appearance and pH results remained consistent throughout the study period. Particulate matter detected was much lower than specified limits.

Another study evaluated drug compatibility/stability when Disodium Levoleucovorin drug product was admixed with either 0.9% Saline or D5W (5% dextrose) in Large Volume Parenteral (LVP) bags. Drug product vials were reconstituted with 0.9% Saline or D5W in LVP bags, stored at 20-25° C., and tested at initial, 6- and 18-hour intervals against pre-set acceptance limits. Resulting data that showed the drug to be chemically stable in these test conditions through 18 hours. Disodium Levoleucovorin Drug Product (175 mg/vial and 300 mg/vial) was found to be adequately stable in 0.9% Saline and D5W LVP solutions based on the constancy of values for tests conducted on the solutions over an 18-hour period.

Example 8: Microbiological Stability

A microbial hold time study was carried out with Disodium Levoleucovorin for Injection, 300 mg/vial, by preparing 50 mg/mL samples 0.9% Saline and 0.5 mg/mL samples in either 0.9% Saline or D5W. Individual samples were inoculated with either Escherichia coli (E. coli), Staphylococcus aureus (S. aureus), Pseudomonas aeruginosa (P. aeruginosa), Bacillus subtilis (B. subtilis) Candida albicans (C. albicans), or Aspergillus brasiliensis (A. brasiliensis) at concentrations of <100 CFU/mL. Samples were stored at 20-25° C. over a period of 24 hours with testing at initial, 12 hours, and end of the 24-hour study. Microbial enumeration using direct plate method was qualified for each strengths and diluents combination before using it in this study. There was no growth (defined as less than 0.5 log increase in count; expressed as positive log reductions) observed for any organisms over the course of the study.

Based on the chemical and microbiological studies, reconstituted solutions of Disodium Levoleucovorin for Injection diluted as admixtures in 0.9% Saline or D5W are deemed stable and acceptable for use within 12 hours of their preparation when stored at room temperature.

Example 9: Disodium Levoleucovorin Y-Site Compatibility with Co-Administration Drugs The physical compatibility of Disodium Levoleucovorin for Injection, at concentrations of 0.5 mg/mL and 5 mg/mL, was evaluated with a selection of 5 chemotherapeutic drug products, (5-flurouracil, methotrexate, oxaliplatin, docetaxel, and Irinotecan), in a simulated Y-site study. These evaluations were performed in both 0.9% Saline and D5W. The compatibility of Disodium Levoleucovorin with these potential co-administration drugs was tested at the admixed volume ratio 1:1 by visual observation, turbidity, and particulate matter. The admixtures were tested immediately after mixing, and then at 1 and 4 hours thereafter at room temperature.

The admixture of Disodium Levoleucovorin, at both 0.5 mg/mL and 5 mg/mL concentrations, and Oxaliplatin in 0.9% Saline was not performed. Oxaliplatin is incompatible with solutions containing Sodium Chloride, and should never be administered with Disodium Levoleucovorin reconstituted in 0.9% Saline.

In this study, no test drug was found to be incompatible based on turbidity or particulate matter tests. The admixture of all test drugs, with the exception of Irinotecan, did not result in any visual failure. With regards to Irinotecan, there was significant color change after admixture with Disodium Levoleucovorin at 5 mg/ml, diluted in both 0.9% Saline and D5W.

Unless otherwise defined, all technical and scientific terms used herein are accorded the meaning commonly known to one of ordinary skill in the art.

Those skilled in the art will recognize, or be able to ascertain using no more than routine experimentation, numerous equivalents to the specific procedures, embodiments, claims, and examples described herein. Such equivalents are intended to be encompassed by the following claims.

It is to be understood that wherever values and ranges are provided herein, all values and ranges encompassed by these values and ranges, or a combination of these values and ranges, are meant to be encompassed within the scope of the aspects and embodiments provided herein. Moreover, all values that fall within these ranges, as well as the upper or lower limits of a range of values, are also contemplated by the present application.

The invention claimed is:

1. A pharmaceutical composition comprising:
a) a lyophilized composition prepared by a process comprising:
1) mixing mannitol and levofolinic acid in sparged water under an inert atmosphere, wherein the ratio of mannitol to levofolinic acid is 3:5 w/w;
2) adding aqueous sodium hydroxide to the levofolinic acid and mannitol mixture;
3) filtering the solution; and
4) lyophilizing the filtered solution such that the lyophilized composition is prepared; wherein the composition comprises 10-formyldihydrofolic acid; and 4-aminobenzoylglutamic acid,
wherein the 10-formyldihydrofolic acid is not more than 0.5% of the mole fraction of the composition, and wherein the temperature of the mixture is maintained at about 15° C. to 17° C. during steps 1) through 3).

2. The composition of claim 1, wherein the 10-formyldihydrofolic acid is not more than about 0.4% mole fraction of the composition.

3. The pharmaceutical composition of claim 1, wherein the pharmaceutical composition is suitable for injection.

4. The pharmaceutical composition of claim 3, wherein the injectable pharmaceutical composition has a pH of about 7.5 to 8.1.

5. The composition of claim 1, wherein the composition is dissolved in a diluent.

6. The composition of claim 5, wherein the diluent is 0.9% saline or 5% dextrose.

7. The composition of claim 5, wherein the composition comprises about 50 mg/mL of levofolinic acid.

8. The composition of claim 1, wherein the composition comprises about 175 mg of levofolinic acid.

9. The composition of claim 1, wherein the composition comprises about 300 mg of levofolinic acid.

10. The pharmaceutical composition of claim 3, wherein the injectable pharmaceutical composition has a pH of about 7.0 to 8.5.

11. The pharmaceutical composition of claim 3, wherein the injectable pharmaceutical composition has a pH of about 7.4 to 8.1.

12. The pharmaceutical composition of claim 3, wherein said injection is intramuscular, intravenous, subcutaneous, or a combination thereof.

13. The pharmaceutical composition of claim 12, wherein said injection is intramuscular.

14. The pharmaceutical composition of claim 12, wherein said injection is intravenous.

15. The pharmaceutical composition of claim 12, wherein said injection is subcutaneous.

* * * * *